United States Patent [19]

Burke

[11] Patent Number: 5,352,686
[45] Date of Patent: Oct. 4, 1994

[54] METHOD FOR PRODUCING AN OREXIGENIC EFFECT

[75] Inventor: John T. Burke, Cincinnati, Ohio

[73] Assignee: Merrell Dow Pharmaceuticals Inc., Cincinnati, Ohio

[21] Appl. No.: 97,097

[22] Filed: Jul. 26, 1993

Related U.S. Application Data

[63] Continuation of Ser. No. 742,951, Aug. 9, 1991, abandoned.

[51] Int. Cl.$^5$ ............................................. A61K 31/44
[52] U.S. Cl. ................................... 514/306; 514/910
[58] Field of Search ......................... 514/306, 340, 410

[56] References Cited

U.S. PATENT DOCUMENTS 4,906,755  3/1990  Gittos .................................... 546/94

OTHER PUBLICATIONS

Acta Psychiatrica Scandinavica, vol. 82, Supplement 361, 1990, O. Trygstad: Drugs in the Treatment of Bulimia Nervosa, pp. 34–37.
Journal of the American Dietetic Association, Nov. 1989; vol. 89; L. G. Tolstoi: The role of Pharmacotherapy in anorexia nervosa and Bulimia, pp. 1640–1646.
Psychiatric Developments, vol. 1, No. 3, 1983, K. A. Halmi: The State of Research in Anorexia Nervosa and Bulimia, pp. 247–262.
Annals of the New York Academy of Sciences, vol. 600, The Neuropharmacology of Serotonin, Serotonin and Appetite, G. Curzon, pp. 521–531 (1990).
Annals of the New York Academy of Science, vol. 600, The Neuropharmacology of Serotonin, Serotonin in Human Eating Disorders, David C. Jimerson, et al, pp. 532–545 (1990).
Hibert et al, Conformation–Activity Relationship Study of 5-HT$_3$ Receptor Atagonists and a Definition of a Model for this Receptor Site, J. Med. Chem. (1990) 33, 1594–1600.

Primary Examiner—Marianne M. Cintins
Assistant Examiner—T. J. Criares
Attorney, Agent, or Firm—J. Michael Dixon; William R. Boudreaux

[57] ABSTRACT

The present invention is directed to the use of esters of hexahydro-8-hydroxy-2,6-methano-2H-quinolizin-3(4H)-one and hexahydro-8-hydroxy-2,6-methano-2H-quinolizines in the manufacture of a medicament for producing an orexigenic effect.

2 Claims, No Drawings

METHOD FOR PRODUCING AN OREXIGENIC EFFECT

This is a continuation of U.S. patent application Ser. No. 07/742,951, filed Aug. 9, 1991, now abandoned.

The present invention is directed to a new class of orexigenic agents.

In accordance with the present invention, a new class of orexigenic agents have been discovered which can be described by the following formula:

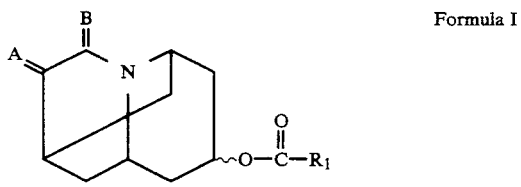

Formula I wherein A is $H_2$, O, (H)(OH), $(OH)_2$ or N—OH; B is $H_2$, $(H)(CH_3)$, $(H)(CH_2NR_3R_4)$ or $CH_2$ wherein $R_3$ and $R_4$ are $C_{2-4}$ alkyl or are combined to give tetramethylene, pentamethylene or —$CH_2CH_2$—O—$CH_2CH_2$—; $R_1$ is

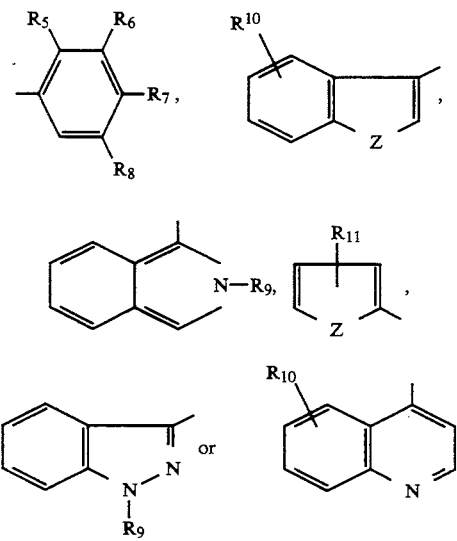

wherein Z is $NR_9$, O or S; $R_5$, $R_6$, and $R_8$ are each hydrogen, halogen, $C_{1-3}$ alkyl or $C_{1-3}$ alkoxy; $R_7$ is hydrogen, amino, $(C_{1-4}$ alkyl)amino, $(C_{1-4}$ alkyl)$_2$amino, alkoxy or nitro; $R_9$ is hydrogen, $C_{1-4}$ alkyl or phenyl $(C_{1-2}$ alkyl); $R_{10}$ is hydrogen, halogen, $C_{1-4}$ alkyl, $C_{1-4}$ alkoxy, hydroxy, cyano or -$CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quaternary ammonium salts of the aforesaid compounds.

The compounds of Formula I are orexigenic agents. They can be utilized to stimulate the appetites of patients suffering from anorexia due to chronic medical conditions, eating disorders, and other conditions in which excessive weight loss has produced a detrimental effect on the patients' health.

Examples of the $C_{1-4}$ alkyl groups referred to above are methyl, ethyl, propyl, isopropyl and butyl. Examples of the $C_{1-4}$ alkoxy groups are methoxy, ethoxy, propoxy and butoxy. The halogens referred to above can be fluorine, chlorine or bromine. When the wavy line in the general structural formula is changed to a solid line, this indicates that the configuration of the compounds is endo. Such endo-compounds can also be referred to as trans. Similarly, exo-compounds can also be referred to as cis. Any hydrates of the present compounds are considered as equivalent to the compounds themselves and this would include compounds in which the carbonyl (i.e., A is O) exists as $(OH)_2$.

A preferred group of compounds for use in the present invention are those wherein the ester is attached to the polycyclic ring in the endo-configuration. A further preferred group are those having the endo-configuration wherein A is =O and =$(OH)_2$. In a still further preferred group, B is additionally =$H_2$.

The pharmaceutically acceptable acid addition salts referred to above can be non-toxic salts with suitable acids such as those with inorganic acids, for example hydrochloric, hydrobromic, nitric, sulfuric or phosphoric acids; or with organic acids such as organic carboxylic acids, for example, acetic, propionic, glycolic, maleic, hydroxymaleic, tartaric, citric, salicyclic, 2-acetyloxybenzoic, nicotinic or isonicotinic; or organic sulfonic acids, for example methanesulfonic, ethanesulfonic, 2-hydroxyethanesulfonic, 4-toluenesulfonic or 2-naphthalensulfonic. Quaternary ammonium salts are formed with alkyl halides such as methyl chloride, methyl bromide or ethyl bromide; or with sulfate esters such as methyl 4-toluenesulfonate or methyl 2-naphthalenesulfonate.

Some specific examples of compounds encompassed by the present invention are the following:

endo-8-(3,5-Dimethylbenzoyloxy)hexahydro-2,6-methano-2H-quinolizin-3(4H)-one exo-8-(3,5-Dimethylbenzoyloxy)hexahydro-2,6-methano-2H-quinolizin-3(4H)-one endo-8-(3,5-Dichlorobenzoyloxy)hexahydro-2,6-methano-2H-quinolizin-3(4H)-one endo-8-(3,5-Dimethoxybenzoyloxy)hexahydro-2,6-methano-2H-quinolizin-3(4H)-one endo-8-(4-Aminobenzoyloxy)hexahydro-2,6-methano-2,6H-quinolizin-3(4H)-one endo-8-(4-Dimethylaminobenzoyloxy)hexahydro-2,6-methano-2H-quinolizin-3(4H)-one endo-8--(3,5-Dimethylbenzoyloxy)octahydro-2,6-methano-2H-quinolizine endo-8-(3-Indolylcarbonyloxy)octahydro-2,6-methano-2,6-methano-2H-quinolizine endo-8-(5-Cyano-3-indolylcarbonyloxy)hexahydro-2,6methano-2H-quinolizin-3(4H)-one endo-8-(3,5-Dichlorobenzoyloxy)hexahydro-2,6-methano-4methyl-2H-quinolizin-3(4H)-one endo-8-(3-Indolylcarbonyloxy)hexahydro-4-(diethylaminomethyl)-2,6-methano-2H-quinolizin-3(4H)-one endo-8-(3-Indolylcarbonyloxy)-3-hydroxyimino-2,6-methanooctahydro-2H-quinolizine endo-8-(2-Methyl-1-isoindolycarbonyloxy)hexahydro-2,6-methano-2H-quinolizin-3(4H)-one endo-8-(2-Pyrrolidinylcarbonyloxy)hexahydro-2,6-methano 2H-quinolizin--3(4H)-one endo-8-(3-Indolylcarbonyloxy)-2,6-methanooctahydro-2H-quinolizin-3-ol endo-Hexahydro-8-(1-methyl-3-indazolylcarbonyloxy)-2,6methano-2H-quinolizin-3(4H)-one endo-Hexahydro--8-(3-indazolylcarbonyloxy)-2,6-methano-2H-quinolizin-3(4H)-one.

Methods for producing the compounds of Formula I are known in the art. For example, see U.S. Pat. Nos, 4,9006,755 or 5,011,846 which are hereby incorporated by reference. The '755 and '846 patents specify that the compounds of Formula I are serotonin 5HT3 antagonists and that they are useful in the treatment of a number of disease states such as migraine, emesis, glaucoma, psychosis, anxiety, and gastric immotility.

As noted above, a new therapeutic use has been found for these compounds. It has been discovered that these compounds produce an orexigenic effect. The compounds will be useful in a number of clinical situations in which loss of appetite and excessive weight loss is producing a detrimental effect upon the patients' overall health. The compounds of Formula I will stimulate these patients' appetites thereby either increasing or stabilizing the patients' body weight. The compounds will alleviate the patients' malnourished state which is exacerbating the underlying disease the patient is suffering from. Examples of conditions in which patients may experience anorexia and an unacceptable weight loss include anorexia nervousa, depression, anxiety, various endocrinopathies, chronic liver disease, chronic kidney disease, cancer, AIDS, cachexia, etc. Patients undergoing cancer chemotherapy often experience significant weight loss due to anorexia. Other conditions in which anorexia is producing malnourishment will be readily apparent to those skilled in the art.

The quantity of compound required to produce the orexigenic effect described above will vary with the particular compound utilized, the patient, the route of administration, the severity of the patient's condition, the presence of other underlying disease states in the patient, and other medications which are being administered concurrently to the patient. Generally though, the compounds will produce an orexigenic effect at a dosage range of from 0.01 to 100 mg/kg/day. The compounds will typically be administered from 1-4 times daily. po The preferred orexigenic agents of the instant invention are endo-hexadro-8-(3-indolylcarbonyloxy)-2,6-methano-2H-quinolizin-3(4H)-one and endo-8-(3-indolylcarbonyloxy)-2,6-methanooctahydro-2H-quinolizin-3-ol.

As used in this application:

a) the term "patient" is taken to mean warm-blooded animals, such as mammals; for example, dogs, rats, mice, cats, guinea pigs, horses, cattle, sheep and primates, including humans.

b) the term "orexigenic effect" refers to the ability of the compounds to stimulate a patient's appetite thereby relieving or alleviating the patient's excessive weight loss and accompanying malnourished state.

The compounds of Formula I can be administered in various manners to achieve the desired effect. The compounds are typically administered either orally or parenterally (subcutaneously, intravenously, intra-muscularly). They can also be administered by suppository.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

What is claimed:

1. A method for producing an orexigenic effect comprising administering to a patient in need thereof an orexigenic amount of endo-hexadro-8-(3-indolycarbonyloxy)-2,6-methano-2H-quinolizin-3(4H-one.

2. A method for producing an orexigenic effect comprising administering to a patient in need thereof an orexigenic amount of endo-8-(3-indolylcarbonyloxy)-2,6-methanooctahydro-2H-quinolizin-3ol.

* * * * *